United States Patent [19]
Sisto et al.

[11] Patent Number: 5,849,795
[45] Date of Patent: Dec. 15, 1998

[54] TACHYKININS ANTAGONISTS

[75] Inventors: Alessandro Sisto; Edoardo Potier, both of Rome; Stefano Manzini, Florence; Christopher Fincham, Pomezia; Paolo Lombardi, Cesate; Federico Arcamone, Nerviano, all of Italy

[73] Assignee: A Menarini Industrie Farmaceutiche Riunite S.r.l., Florence, Italy

[21] Appl. No.: 926,103

[22] Filed: Sep. 9, 1997

Related U.S. Application Data

[62] Division of Ser. No. 676,514, Jul. 8, 1996, Pat. No. 5,698,710.

Foreign Application Priority Data

Jan. 19, 1994 [IT] Italy .................................. FI94A0009

[51] Int. Cl.⁶ .......................... A61K 31/15; C07C 233/65
[52] U.S. Cl. ......................... 514/617; 564/123; 564/149; 564/80; 564/82; 514/616; 514/601
[58] Field of Search ..................................... 564/123, 149, 564/80; 514/617, 616, 601

[56] References Cited

PUBLICATIONS

Villalgordo, J.M. et al.: Reaction of 3–Amino–2H–azirines with 2–Amino–4, 6–dinitrophenol: Synthesis of Quinazoline and 1,3–Benzoxazole Derivatives. Helv. Chim. Acta. vol. 73, pp. 959–974, 1990.

Crisma, M. et al: Structural Versatility of Peptides from $C^\alpha$–Dialkylated Glycines. Macromolecules, vol. 21, pp. 2071–2074, 1988.

*Primary Examiner*—Alan L. Rotman
*Assistant Examiner*—Charanjit S. Aulakh
*Attorney, Agent, or Firm*—Abelman, Frayne & Schwab

[57] ABSTRACT

The present invention refers to tachykinins antagonists of general formula (I)

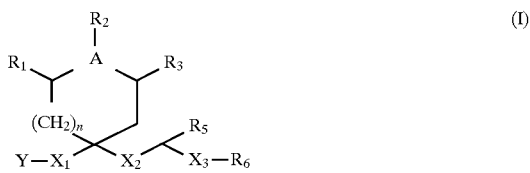

their preparation and pharmaceutical compositions containing them.

4 Claims, No Drawings

TACHYKININS ANTAGONISTS

This is a division of application Ser. No. 08/676,514, filed as PCT/EP95/00193, Jan. 19, 1995 now U.S. Pat. No. 5,698,710.

This is a continuation-in-part of International Application PCT/EP95/00193 having an international filing date of Jan. 19, 1995.

FIELD OF THE INVENTION

The present invention refers to tachykinins antagonists of general formula (I)

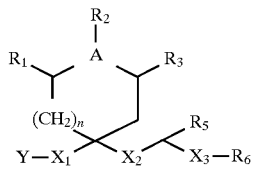

wherein:

Y is chosen in the group consisting of aryl-, aryl-alkyl-radical containing from 7 to 12 carbon atoms wherein the aryl moiety is selected out of a group consisting of pyridine, pirrole, biphenyl, benzene, naphtene, tetrahydroquinoline, quinoline, imidazole, furan, thiophene, indan possibly substituted on the ring with one or more substituents independently chosen from halogen, alkyl-radical containing from 1 to 6 carbon atoms possibly substitued with no more than three fluorine atoms (for example trifluoromethyl group), oxyalkyl-radical containing from 1 to 6 carbon atoms, possibly substituted with no more than three fluorine atoms (for example trifluoromethoxyl group), $-NH_2$, $-NHR_{10}$, $-OR_{10}$, $-N(R_{10})_2$, $-CONHR_{10}$, $-COR_{10}$, $-COOR_{10}$, $-R_{10}COOR_{11}$, $-OR_{10}COOR_{11}$, $-CONHR_{10}$, $-R_{10}CONHR_{11}$, $-NHCOR_{10}$, nitro-radicals wherein $R_{10}$ and $R_{11}$ are hydrogen or an alkyl-radical, linear or branched, containing from 1 to 6 carbon atoms, with the proviso that $R_{10}$ cannot be H in the case of $R_{10}COOR_{11}$, $OR_{10}COOR_{11}$ and $R_{10}CONHR_{11}$ or Y is a radical of formula:

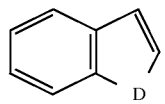

wherein D=O, S, $CH_2$ and N—$R_4$ wherein $R_4$ is chosen in the group constitued by hydrogen, an akyl-radical, linear or branched, containing from 1 to 6 carbon atoms, an acyl-radical $R_9$—CO, wherein $R_9$ is hydrogen or an akyl-chain containing from 1 to 3 carbon atoms;

$X_1$ and $X_2$, same or different from each other, are chosen in the group consisting of —$CONR_8$, —$NR_8CO$—, —$CH_2NR_8$—, wherein $R_8$ is chosen in the group consisting of hydrogen or an alkyl-chain, linear or modified, containing from 1 to 6 carbon atoms;

$X_3$ is chosen in the group consisting of —$CONR_7$, —$NR_7CO$— and $R_7$ is chosen in the group consisting of an alkyl-radical with no more than 15 carbon atoms;

$R_1$, $R_2$ and $R_3$ independently from each other are hydrogen, halogen, $OR_{12}$ wherein $R_{12}$ is chosen in the group consisting of hydrogen, —$CH_2O(CH_2)_2OCH_3$ or —$CH_2O(CH_2)_2OCH_2CH_3$; A can be N, S, O or CH; n is a number from 0 to 2;

$R_5$ and $R_6$ are chosen, independently from each other, in the group consisting of aryl-alkyl-radical containing no more than 15 carbon atoms, wherein the aryl moiety is selected out of the group consisting of pyridine, pirrole, benzofurane, biphenyl, benzene, indole, naphtene, tetrahydroquinoline, imidazole, quinoline, furane, thiophene, indan, possibly substituted on the ring with one or more substituents chosen independently from each other from halogen, alkyl-radical containing from 1 to 6 carbon atoms, possibly substituted with no more than three fluorine atoms (for example trifluoromethyl group), oxyalkyl-radical containing from 1 to 6 carbon atoms, possibly substituted with no more than three fluorine atoms (for example trifluoromethoxyl group), an $-NH_2$, $-NHR_{11}$, $-OR_{10}$, $-N(R_{10})_2$, $-CONHR_{10}$, $-COR_{10}$, $-COOR_{10}$, $-R_{10}COOR_{11}$, $-OR_{10}COOR_{11}$, $-R_{10}COR_{11}$, $-CONHR_{10}$, $-R_{10}CONHR_{11}$, $-NHCOR_{10}$, nitro-radicals, wherein $R_{10}$ and $R_{11}$ are hydrogen or an alkyl-radical, linear or branched, containing from 1 to 6 carbon atoms, with the proviso that $R_{10}$ can not be H in the case of $R_{10}COOR_{11}$, $OR_{10}COOR_{11}$ and $R_{10}CONHR_{11}$.

The invention refers also to the process for their preparation and to pharmaceutical compositions containing them.

STATE OF THE ART

Tachykinins are a family of at least three peptides, known as Substance P. Neurokinin A (NKA) and Neurokinin B (NKB).

The research in the field of tachykinins antagonists, initially based principally on single or multiple substitutions of the amino acids present in the sequence of peptidic-agonists of Substance P and of the other tachykinins, brought to the discovery of nonapeptides containing one or more units of D-triptophane (Regoli et al. Pharmacol. 28, 301 (1984)). On the other hand the probelms connected with the use as pharmaceuticals products of peptides presenting an high molecular weight (multiplicity of enzymatic hydrolytic attack sites, poor bioavailability, rapid excretion by the liver and kidneys) spurred to search for the smallest peptide fragment still capable of exerting an antagonistic action. These studies brought to the singling out of tri-and di-peptides, suitably substituted, antagonist of Substance P (EP-333 174 and EP-394 989).

Recently non-peptidic antagonists were reported which do not present the drawbacks of the metabolic instability of peptides (WO 94/13694): The compounds of the present invention show antagonism against Substance P, Nurokinin A and Neurokinin B.

Therefore, the above said compounds can be used as pharmaceutical compounds in the treatment and prevention of those disorders wherein the tachykinins Subtance P, Neurokinin A and Neurokinin B play a role as neuromodulators.

The compounds of formula (I) are useful for the treatment of disorders wherein the tachykinins play a patogenic role in particular in the treatment of artritis, asthma, inflammations, tumoral growth, Huntington's disease, neuritis, neuralgia, migraine, hypertension, incontinence of urine, urticaria, carcinois syndrome symptoms, influenza and cold, disorders related to the immuno system.

By way of example, reference can be made to patologies of the respiratory system as asthma, allergic rhinitis; ophthalmic system as conjunctivitis; cutaneous system as allergic dermatitis, dermatitis by contact, psoriasis; intestinal system as ulcerative colitis and Chron's disease.

DETAILED DESCRIPTION OF THE INVENTION

It was surprisingly found, and this is a fundamental characteristic of the present invention, that non-peptidic compounds of general formula (I), as previously defined, show better inhibition of the tachykinins bond to the NK1 receptor and high metabolic stability.

In particular, a preferred group of compounds of the present invention comprises the compounds of formula (I) wherein:

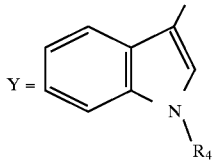

wherein $X_1$=—CONH—, $X_2$=—CONH— and $X_3$=—CONCH$_3$— and wherein $R_1, R_2, R_3, R_4, R_5, R_6, R_7, R_9, R_{10}, R_{11}$ and A are as above defined. Particularly preferred are the compounds of formula (I) wherein:

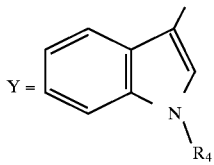

wherein $X_1$=—CONH—, $X_2$=—CONH— and $X_3$=—CONCH$_3$—, $R_5$=2-methylnaphthyl and $R_6$=benzyl.

In the present invention the alkyl-radical is preferably chosen in the group of: methyl, ethyl, propyl, butyl and pentyl; the aryl-, alkyl-aryl and aryl-alkyl-radical preferably presents an alkyl-radical as above defined while the aryl moiety is preferably pyridine, pirrole, benzofuran, biphenyl, benzene, indole, naphtalene, tetrahydroquinoline, imidazole, tetrahydroindoline, quinoline, thienyl, furan, thiofene, indan, possibly substituted as above defined. As oxyalkyl-radical is preferred a: methyloxy, ethyloxy, propyloxy, trifluoromethyloxy, while as alkyl radicals methyl and trifluoromethyl are preferred.

Halogen, as used herein, means fluorine, chlorine, bromine and iodine and the groups substituted with no more than three fluorine atoms are preferably tri-substituted.

In view of the asymmetry centres of formula (I), the invention refers to the various diastereoisomers of said formula, in particular the substituent $R_5$ is preferably in the S-configuration.

The compounds of general formula (I), as above defined, are prepared according to the following reaction paths and description, wherein, if not otherwise indicated, $R_1, R_2, R_3, R_4, R_5, R_6, R_7, R_8, R_9, R_{10}, R_{12}, A, X_1, X_2, X_3$ are as above defined.

a) By condensation, in the presence of a suitable condensing agent, of the intermediate of formula (II), wherein $X_4$ is COOH or NH$_2$:

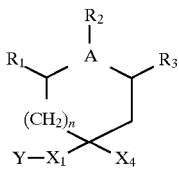

with the intermediate of formula (III), wherein $X_5$ is NH$_2$ when $X_4$ is COOH, while when $X_4$ is NH$_2$, $X_5$ e COOH:

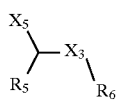

The intermediate of general formula (II) is prepared for example according to Scheme 1.

Such Scheme shows the preparation of an intermediate of general formula (IIa) wherein $X_1$ is —CH$_2$—N(Prot$_2$)—, by reductive amination of a compound of general formula (V), as above defined, and an aldehyde of general formula Y—CHO with sodium cyanoborohydride or sodium borohydride to give the corresponding intermediate of general formula (VI); this reaction is preferably carried out in acetic acid or alcohol at room temperature, maintaining the pH slightly acid, preferably at pH 4.5. The intermediate (VI) is substituted, giving the intermediate (VII), in order to protect the amino group, and the ester is finally splitted by basic hydrolysis; preferably the group introduced is the tert-butyloxycarbonyl-group, and such reaction was carried out with ditert-butylcarbonate in aprotic polar solvents, preferably tetrahydrofuran, at room temperature.

Such intermediate of general formula (III) is prepared, for example, according to Scheme 2.

Scheme 2 describes the preparation of an intermediate of general formula IIIa, wherein $X_3$=NR$_7$CO and $R_6, R_5, R_7$ are as above defined, HX is an acid chosen in the group: acetic acid, chloridric acid, sulfuric acid, trifluoroacetic acid and the configuration of the carbon atom to which group $R_5$ is linked is preferably S. Such intermediate is prepared by reaction between the D-amino acid derivative of general formula (VIII), commercialy available or prepared as described in the examples, or by any other synthetic way obvious for the man skilled in the art, and the alkyl-halogenide of general formula R$_7$-Hal, wherein Hal is chosen in the group of chlorine, iodine or bromine and $R_7$ is as above described, in the presence of a base, chosen in the group of alkaline- or earth-alkaline-hydrides in an inert, aprotic, polar solvent, for example tetrahydrofuran or dioxane. In particular the reaction is performed at 0° C. in tetrahydrofuran using as base sodium-hydride and as alkylating agent methyl iodide. The following reaction with the ammonium salt of hydroxybenzotriazole, carried out in the presence of a suitable condensing agent, gives the corresponding amide (X); the latter by reaction with bis (trifluoracetoxy)iodobenzene produces the gem-diamine derivative (IIIa); such reaction is carried out at room temperature in a water/acetonitrile mixture.

Another synthesis-path, known by the man skilled in the art, is the sequential condensation on the intermediate of general formula (III), as above defined, of the two residues of general formula (XI) and (XII)

Y—COOH (XII)

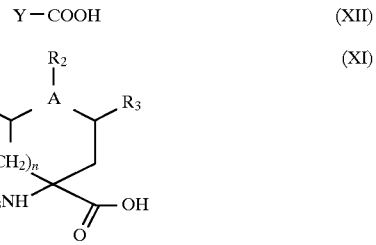

After the condensation of the first fragment (XI), the elimination of the protecting group Prot$_3$, allows the liberation of the amino-group and the subsequent condensation of fragment (XII), wherein Prot$_3$ is preferably the tert-butyloxycarbonyl-group and the elimination step is an acid lysis, preferably carried out with a saturated solution of hydrochloric acid in organic solvents as ethyle acetate, ethyl ether, dioxane, b) The reaction by-products are eliminated by evaporating the reaction solvent and teating the residue or a solution thereof in a suitable organic solvent with slightly acid or slightly basic solutions.

c) The crude product obtained from step (b) is purified by chromatography or by crystallization.

The above described condensations can be performed according to the information known in literature for peptide-synthesis.

Excellent product yield and purity, were obtained using, as condensing agent, the benzotriazolyloxytripyrrolidine phosphonium hexafluorophosphate PyBop). In particular the reaction was carried out with addition of slight excess of PyBop to a carboxylic component solution, maintained at low temperature, followed by addition of the hydrochloride aminic component and a quantity of tertiary amine of three equivalents in respect to the condensing agent.

An alternative procedure envisages the use, as condensig agent, of 1-ethyl-3-(3'-dimethylaminopropyl)-carbodiimide (WSC.HCl).

For the condensation reaction,which can be preferably carried out at room temperature, the usual polar, aprotic organic solvents chosen in the group of dimethylformamide, dioxane, tetrahydrofuran, methylene chloride, dichloroethane, chloroform are used.

Another object of the present invention are therefore the processes for the preparation of the intermediates of formula (II) and (III) and such intermediates obtained through the above said processes.

The compounds of the present invention can exist in different isomeric configurations. In fact, while the configuration of the carbon atom bound to substituent $R_5$ is univocally predetermined by the amino acid chosen as starting product, the other starting compounds can be a mixture of enantiomers difficult to separate. It follows that the present compounds can be obtained as diastereoisomers mixtures. Said mixtures can be easily resolved by chromatography. In any case compounds of formula (I) can be used both in optically active form and in the form of isomeric mixtures. For their therapeutical use the compounds according to the present invention can be administered parenterally, intranasaly, orally or sublingually. The formulations containing the new compounds can be prepared, according to known techniques, combining the active principle with an inert carrier and possibly with the conventional additives suitably chosen. In view of the oral or sublingual use the present compounds can be administered as tablets, pellets, drops, elixir, ecc., prepared with the conventional carriers/excipients as starch, sugars, water, alcohol ecc. and possibly comprising aromatizing agents, stabilizers, preservatives, lubricants ecc. For parenteral or intranasal administration the preferred carrier is sterilized water for injection. Additives can be added according to the known art.

The therapeutically effective daily dosage can vary according to the subject under treatment (weight, age, disease gravity) and to the administration route. Generally it can be said that the present compounds are active when subministered in a daily dosage of 0.005 to 10 mg/Kg. The pharmaceutical compositions according to the present invention will contain the active product in a suitable quantity in order to allow a correct daily dosage in the above said range, normally by 1–3 administrations per day.

The following example is given for better illustrating the invention.

EXAMPLE $N^\alpha$[N-(1(H)indol-3-yl-carbonyl)-1-amino-cyclohexan-carbonyl]-L-2-naphthylalanine-N-methyl-N-benzylamide [I3c-1-Ac$^6$c-L-2Nal-NMeBz]

For the sake of simplicity the following abreviations were also used: 1-Ac$^6$c, for the 1-amino-cyclohexancarboxylic-acid; I3c, for the 1(H)indol-3-yl-carbonyl-residue; the indications normally used for the peptide synthesis.

1a) To an amino-cyclohexanecarboxylic-acid (1.4 g) in 14 ml of NaOH 2N, cooled at 0° C. under vigorous stirring in nitrogen current, a solution of di-tert-butyl-dicarbonate (9.1 g) in 14 ml of isopropanole was added. The solution was left under stirring at room temperature for 16 hours.

The isopropanole was evaporated in vacuo and the aqueous solution was extracted with ethyl ether (3×50 ml). The aqueous phase was acidified to pH 3 with HCl 1N and extracted with ethyle acetate (3×50 ml). The organic solution was washed with a solution saturate in NaCl (3×50 ml), dried on $Na_2SO_4$ and the solvent was eliminated obtaining 309 mg of $N^\alpha$(tert-butyloxy-carbonyl)-1-aminocyclohexanecarboxylic acid (Boc-1-Ac$^6$c-OH) (yield 47%). TLC [chloroform/methanole 9:1 v/v (CM)]=0.36.

1b) to a solution of $N^\alpha$(tert-butyloxy-carbonyl)-L-2-napthylalanine (500 mg) in 7 ml of anhydrous DCM, at 0° C. under vigorous stirring in nitrogen current, N,N-methylbenzylamine (0.25 ml), N-hydroxybenzotriazolyltripyrrolidine phosphonium hexafluorophasphate (PyBop) (0.998 g) and finally, slowly, DiPEA (0.63 ml) are added. The solution is left under stirring at 0° C. for 30' and at room temperature for 16 hours. The solvent is eliminated by evaporation in vacuo and the residue is collected with EtOAc (50 ml). The organic solution is extracted with an aqueous solution of $NaHCO_3$ (3×50 ml), therefater with an aqueous solution saturated in NaCl (3×50 ml), with an aqueous solution of HCl 0.1N (3×50 ml) and finally again with an aqueous solution saturated in NaCl (3×50 ml). The organic phase is dried on $Na_2SO_4$ and the solvent is eliminated giving a slightly yellow oil which is purified by chromatography on silica using as eluent hexane/ethyle acetate 70:30 (v/v) giving 478 mg of $N^\alpha$(tert-butyloxycarbonyl)-L-2-naphthylalanine-N-methyl-N-benzyl amide (yield 71%).

TLC [chloroform/methyl alcohol 95:5 v/v]=0.85.

for the HPLC a Phase Sep. Spherisorb ODS-2$^R$ 5m 46×250 mm was used and as eluents:

A=0.1 trifluoroacetic acid in acetonitrile

B=0.1 trifluoroacetic acid in water linear gradient of 20% A to 80% A over 25 min; isocratic conditions at 80% of A for 10 min, flow 1 ml/min; determination by UV at 230 nm. Analytical HPLC shows a single peak at $T_R$=28.55 min.

1c) A suspension of the product obtained in the previous step (1b) (0.474 g) in 9 ml of a solution of EtOAc saturated of HCl (about 2N) is left under stirring at room temperature for 30 min. The solvent is eliminated under a slight nitrogen current and the residue is repeatedly suspended in ethyl ethere (4×30 ml), the solvent is eliminated giving 0.400 mg of L-2-naphthylalanine-N-methyl-N-benzyl amide hydrochloride (yield 99%).

TLC [chloroform/methyl alcohol 95:5 v/v): Rf=0.15.

Analytical HPLC in the same conditions given for step (1b) shows a single peak, large, at $T_R$=24.44 min.

1d) To a solution of the compound of step (1a) (0.170 g) in DCM (2 ml) and DMF (0.2 ml), at 0° C. under vigorous stirring in nitrogen current, 0.11 g of HOBt and 0.16 g of WSC.HCl are added. The solution is left under stirring at 0° C. for 30' and therefater 0.25 g of the compound obtained in step (1c) and 0.28 ml of diisopropylethylamine are added.

After 16 hours stirring at room temperature, the solvent was eliminated by evaporation in vacuo and recollected with ethyl acetate. The organic solution is extracted with an aqueous solution of NaHCO$_3$ at 5% (3×50 ml), thereafter with an aqueous solution saturated in NaCl (3×50 ml), then with an aqueous solution of HCl 0.1N (3×50 ml) and finally again with an aqueous solution saturated in NaCl (3×50 ml). The organic phase is dried on Na$_2$SO$_4$ and the solvent is eliminated. The residue is solubilized in 20 ml of an ethyl acetate solution saturated with hydrochloric acid (about 2N). After 1 hour stirring at room temperature, the solvent is evaporated under nitrogen current, the residue is recollected twice with absolute etanole and the solvent is eliminated. The compound is cristallized from carbon tetrachloride giving 320 mg of N$^\alpha$(1-aminocyclohexylcarbonyl)-L-2-naphthylalanine-N-metil-N-benzyl-amine hydrochloride (yield 95%).

TLC [Chloroform/methyl alcohol/acetic acid 85:10:5 v/v): Rf=0.43.

Analytical HPLC in the same conditions as in step (1b) shows a single peak, large, at T$_R$=28.16 min.

1e) A suspension of 3-indolyl-carboxylyc acid (0.125 g) in 1.6 ml of a 1M solution of oxalyl chloride in benzene, cooled at 0° C., is kept under stirring in nitrogen current for 1 hour. After addition of two drops of DMF, the solution, now clear and slightly yellow, is left under stirring at room temperature for another hour. The solvent was eliminated by evaporation under reduced pressure and the residue was recollected with 1 ml of DCM, the resulting solution was added to a solution of the compound obtained in step (1d) (40 mg) and diisopropylethylamine (0.23 ml) in 0.5 ml DCM. The solution was left under stirring at room temperature for 24 hours. After elimination of the solvent under reduced pression, the residue was recollected in ethyl acetate (5 ml) and extracted with an aqueous solution of 5% NaHCO$_3$ (3×50 ml), then with an aqueous solution saturated in NaCl (3×50 ml), with an aqueous solution of HCl 0.1N (3×50 ml) and finally with an aqueous solution saturated of NaCl (3×50 ml). The organic phase is dried over Na$_2$SO$_4$ and the solvent is eliminated. The product is isolated by reversed-phase chromatography on a Hibar Merck column filled with Lichrosorb RP-18$^R$ (7 ml), eluting with isocratic at 65% of A (eluent of step 1b), flow 8 ml/min. The fractions corresponding to the product peak were pooled, concentrated to small volume under reduced pressure and repeatedly free-dried giving 9 mg of N$^\alpha$[N-(1(H)indol-3-yl-carbonyl)-1-amino-cyclohexancarbonyl]-L-2-naphthylalanine-N-methyl-N-benzyl amide.

Analytical HPLC, in the same conditions described for step (1b) shows a single peak at T$_R$=27.71 min.

Operating as above described the following compounds were obtained:

i) 1-N-[N(1(H)indol-3-yl-carbonyl)-1-amino-cyclohexancarbonyl]-amino-1-[N(methyl)N(2-phenylacetyl)]amino-2-phenylethane ii) 1-[N(1(H)indol-3-yl-carbonyl)-1-amino-cyclohexancarbonyl]-amino-1[N-(2-phenylacetyl)amino]-2-(2-naphthyl)ethane iii) 1-N-[N(benzoyl)-1-amino-cyclohexancarbonyl]-amino-1-[N(methyl)N(2-phenylacetyl)]amino-2(2-naphthyl)ethane iv) 1-N-[N(4-methyl-benzoyl)-1-amino-cyclohexancarbonyl]-amino-1-[N(methyl)N(2-phenylacetyl)]amino-2(2-naphthyl)ethane v) 1-N-[N(4-metoxy-benzoyl)-1-amino-cyclohexancarbonyl]-amino-1-[N(methyl)N(2-phenylacetyl)]amino-2(2-naphthyl)ethane vi) 1-N-[N($^4$-chloro-benzoyl)-1-amino-cyclohexancarbonyl]-amino-1-[N(methyl)N(2-phenylacetyl)]amino-2(2-naphthyl)ethane vii) 1-N-[N(3,4-chloro-benzoyl)-1-amino-cyclohexancarbonyl]-amino-1-[N(methyl)N(2-phenylacetyl)]amino-2(2-naphthyl)ethane viii) 1-N-[N(1(methyl)indol-3-yl-carbonyl)-1-amino-cyclohexancarbonyl]-amino-1-[N(methyl)N(2-phenylacetyl)]amino-2(2-naphthyl)ethane ix) 1-N-[N(1(H)indol-3-yl-methyl)-1-amino-cyclohexancarbonyl]-amino-1-[N(methyl)N(2-phenylacetyl)]amino-2(2-naphthyl)ethane x) 1-N-[N(1(methyl)indol-3-yl-carbonyl)-N-methyl-1-amino-cyclohexancarbonyl]-amino-1-[N(methyl)N(2-phenylacetyl)]amino-2(2-naphthyl)ethane xi) 1-N-[N(1(H)indol-3-yl-carbonyl)-1-amino-cyclohexancarbonyl]-amino-1-[N(methyl)N(2-phenylacetyl)]amino-2(p-methoxy)phenylethane xii) N-[N(1(methyl)indol-3-yl-carbonyl)-N-methyl-1-amino-cyclohexancarbonyl]-2 naphthylalanine-N-methyl-N-benzylamide xiii) 1-N-[N(1(H)indol-3-yl-carbonyl)-1-amino-cis-4-hydroxy-cyclohexancarbonyl]-amino-1-[N(methyl)N(2-phenylacetyl)]-amino-2-phenylethane xiv) 1-[N-(1(H)indol-3-yl-carbonyl)-1-amino-trans-4-hydroxy-cyclohexancarbonyl]-amino-1-[N(methyl)N(2-phenylacetyl)]-amino-2-(2-naphthyl)ethane xv) 1-N-[N(1(H)indol-3-yl-carbonyl)-1-amino-cis-4-methoxyethoxymethoxyl-cyclohexancarbonyl]-amino-1-[N(methyl)N(2-phenylacetyl)]-amino-2-phenylethane xvi) 1-[N(1(H)indol-3-yl-carbonyl)-1-amino-trans-4-methoxyethoxymethoxyl-cyclohexancarbonyl]-amino-1-[N(methyl)N(2-phenylacetyl)]-2(2-naphthyl) ethane xvii) N-[N(1(H)indol-3-yl-carbonyl)-1-amino-cis-4-hydroxy-cyclohexancarbonyl]-2-naphthylalanine-N-methyl-N-benzylamide xviii) N-[N(1(H)indol-3-yl-carbonyl)-1-amino-trans-4-hydroxy-cyclohexancarbonyl]-2-naphthylalanine-N-methyl-N-benzylamide xix) N-[N(1(H)indol-3-yl-carbonyl)-1-amino-cis-4-methoxyethoxymethoxyl-cyclohexancarbonyl]-phenylalanine-N-methyl-N-benzylamide xx) N-[N(1(H)indol-3-yl-carbonyl)-1-amino-trans-4-methoxyethoxymethoxyl-cyclohexancarbonyl]-phenylalanine-N-methyl-N-benzylamide xxi) N-[N(1(H)indol-3-yl-carbonyl)-1-amino-4-dimethoxy-cyclohexancarbonyl]-2-naphthylalanine-N-methyl-N-benzylamide xxii) N-[N(1(H)indol-3-yl-carbonyl)-1-amino-4-di (methoxyethoxymethoxy)-cyclohexancarbonyl]-2-naphthylalanine-N-methyl-N-benzylamide xxiii) 1-[N(1(H)indol-3-yl-carbonyl)-4-amino-tetrahydropyranyl-4-carbonyl]-amino-1[N(methyl)-N(2-phenylacetyl)]-amino-2-(2-naphthyl)ethane xxiv) N-[N(1(H)indol-3-yl-carbonyl)-4-amino-tetrahydropyranyl-4-carbonyl]-2-naphthylalanine-N-methyl-N-benzylamide xxv) 1-[N(1(H)indol-3-yl-carbonyl)-4-amino-piperidin-4-carbonyl]-amino-1[N(methyl)-N(2-phenylacetyl)]-amino-2-(2-naphthyl)ethane xxvi) N-[N(1(H)indol-3-yl-carbonyl)-4-amino-piperidin-4-carbonyl]-2-naphthylalanine-N-methyl-N-benzylamide.

The evaluation of the antagonist acivity of NK1 receptors was performed with binding and functional tests.

[$^3$H]SP binding assay in IM9 Cell Line.

The assay was carried out on intact cells as described by Payan et al. (1984). The cells were washed with buffer A at pH 7.5 containing (in mM) Tris-HCl 50, NaCl 150 and 0.02% BSA, thereafter were resuspended in a dosage buffer (buffer A added with protease inhibitors), concentration $1 \times 10^7$ cells/ml. The cells were incubated with [$^3$H]SP in a final volume of 0.5 ml for 60' at room temperature. The non-specific binding was calculated in the presence of 10 mM of non-radioactive SP. The dosage mixture was poured in test tubes for microcentrifugation which were preadsorbed in a solution of BSA 0.5% for at least 3 hours. [$^3$H]SP, free and binded, was separated by cell sedimentation with a microcentrifuge (6 min at 12000 g); the supernatant was removed by aspiration. For competitive tests, the cells IM9 were incubated in triplicate with 0.3 nM of [$^3$H]SP (average value of Kd calculated in saturation experiments) and the competitive ligands were added at six different concentrations (with dilution 1:10 in the dosage buffer) in order to obtain a complete competition curve. The affinity was measured as pKi.

Measurement of pA2 in isolated guinea pig ileum

Male guinea pigs weighing 300–350 g were sacrificed. A ring of ileum (about 3 mm width) deprived of the plexus myentericus, was excised and placed in oxygenated Krebs solution containing 10 μM indomethacin. The sample is mounted on steel hooks and connected with an isotonic transductor (charge 5 mN). After 90 minutes equilibration a cumulative curve for the agonist ([Sar$^9$]Substance P sulphone) was determined. After two or more reproducible curves for the agonist had been obtained, the compound to be tested was added to the bath and a new curve for the agonist was determined in its presence. pA2 values were calculated by using the constrained Schild plot method.

The data in Table I were obtained for compounds of general formula (I).

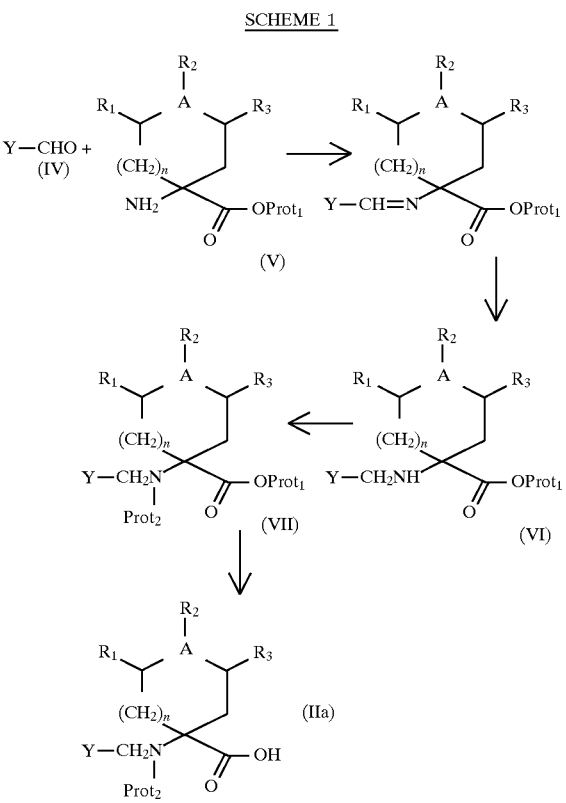

SCHEME 1

Activity of compounds expressed as Affinity (pKi) in the IM9 binding test

| Compound | Example | pKi |
|---|---|---|
| 1-N-[N(1(H)indol-3-yl-carbonyl)-1-amino-cyclohexancarbonyl]-2-(2-naphthyl)alanine-N-methyl-N-benzylamide | example | 9 |
| 1-N-[N(1(H)indol-3-yl-carbonyl)-1-amino-cyclohexancarbonyl]-amino-1[N(2-phenylacetyl)]amino-2(2-naphtyl)ethane | ii | 7.8 |
| N-[N(1(methyl)indol-3-yl-carbonyl)-N-methyl-1-amino-cyclohexancarbonyl]-2-(2-naphthyl)alanine-N-methyl-N-benzylamide | xii | 7.8 |
| N-[N(1(H)indol-3-yl-carbonyl)-1-amino-cis-4-hydrohy-cyclohexancarbonyl]-2-(2-naphthyl)alanine-N-methyl-N-benzylamide | xviii | 8.3 |
| N-[N(1(H)indol-3-yl-carbonyl)-1-amino-trans-4-hydrohy-cyclohexancarbonyl]-2-(2-naphthyl)alanine-N-methl-N-benzylamide | xix | 8.3 |
| N-[N(1(1H)indol-3-yl-carbonyl)-1-amino-cis-4-methoxyethoxymethoxyl-cyclohexancarbonyl]-penylalanine-N-methyl-N-benzylamide | xxv | 7.6 |
| N-[N(1(H)indol-3-yl-carbonyl)-4-amino-tetrahydropyran-4-carbonyl]-2-napthylalanine-N-methyl-N-benzylamide | xxvii | 8.2 |
| 1-N-[N(1(H)indol-3-yl-carbonyl)-4-amino-piperidin-4-carbonyl]-amino-1-[N(methyl)-N-(2-phenylacetyl)]amino-2-naphtyl)ethane | xxviii | 7.9 |
| N-[N(1(methyl)indol-3-yl-carbonyl)-1-amino-cyclohexancarbonyl]-2-(2-naphthyl)alanine-N-methyl-N-benzylamide | | 7.8 |
| N-[N(1(H)indol-3-yl-carbonyl)-4-amino-piperidin-4-carbonyl]-2-(2-naphthyl)alanine-N-methyl-N-benzylamide | | 7.9 |
| N-[N-benzofuran-2-yl-carbonyl)-1-aminocyclohexancarbonyl]-2(2-naphthyl)alanine-N-methyl-N-benzylamide | | 7.35 |
| N-[N(benzoyl)-1-amino-cyclohexancarbonyl]-2-(2-naphthyl)alanine-N-benzylamide | | 7.8 |
| N-[N(4-methoxy-benzoyl)-1-amino-cyclohexancarbonyl]-2-(2-naphthyl)alanine-N-methyl-N-benzylamide | | 7.7 |
| N-[N(4-chloro-benzoyl)-1-amino-cyclohexancarbonyl]-2-(2-naphthyl)alanine-N-methyl-N-benzylamide | | 8 |
| N-[N(3,4-dichloro-benzoyl)-1-amino-cyclohexancarbonyl]-2-(2-naphthyl)alanine-N-methyl-N-benzylamide | | 8.1 |
| N-[N(4-nitro-benzoyl)-1-amino-cyclohexancarbonyl]-2-(2-naphthyl)alanine-N-methyl-N-benzylamide | | 8.3 |
| N-[N(1(H)indol-3-yl-carbonyl)-1-amino-cyclohexancarbonyl]-tyrosine-N-methyl-N-benzylamide | | 7.7 |
| N-[N(1(H)indol-3-yl-carbonyl)-1-amino-cyclohexancarbonyl]-4-methoxyphenylalanine-N-methyl-N-benzylamide | | 8.4 |
| N-[N(1(H)indol-3-yl-carbonyl-1-amino-cyclohexancarbonyl]-4-nitrophenylalanine-N-methyl-N-benzylamide | | 7.7 |
| N-[N(1(H)indol-3-yl-carbonyl)-1-amino-cyclohexancarbonyl]-phenylalanine-N-methyl-N-benzylamide | | 6.75 |
| N-[N(1(H)indol-3-yl-carbonyl)-1-amino-cyclopentancarbonyl]-phenylalanine-N-methyl-N-benzylamide | | 6.8 |
| N-[N(1(H)indol-3-yl-carbonyl)-1-amino-cyclopentancarbonyl]-2-(2-naphthyl)alanine-N-methyl-N-benzylamide | | 8.6 |
| N-[N(1(H)indol-3-yl-carbonyl)-1-amino-cyclopentancarbonyl]-4-methoxyphenylalanine-N-methyl-N-benzylamide | | 6.1 |
| N-[N(1(H)indol-3-yl-carbonyl)-4-amino-tetrahydrothioyran-4-carbonyl]-2-(2-naphthyl)alanine-N-methyl-N-benzylamide | | 8.3 |

SCHEME 2

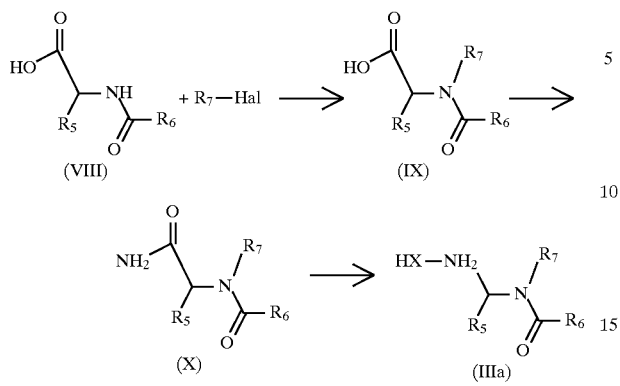

We claim:
1. Tachykinins antagonist of general formula (I)

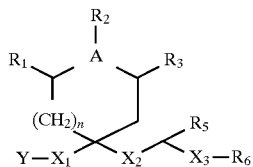

wherein:
Y is benzene optionally substituted with one or more substituents independently selected from the group consisting of halogen, alkyl radicals containing from 1 to 6 carbon atoms optionally substituted with no more than three fluorine atoms, oxyalkyl radicals containing from 1 to 6 carbon atoms, optionally substituted with no more than three fluorine atoms, —$NH_2$, —$NHR_{10}$, —$OR_{10}$, —$N(R_{10})_2$, —$CONHR_{10}$, —$COR_{10}$, —$COOR_{10}$, —$R_{10}COOR_{11}$, —$OR_{10}COOR_{11}$, —NHCOR$_{10}$, nitro-radicals wherein R$_{10}$ and R$_{11}$ are hydrogen or an alkyl radical, linear or branched, containing from 1 to 6 carbon atoms, with the proviso that R$_{10}$ cannot be H in the case of R$_{10}$COOR$_{11}$, OR$_{10}$COOR$_{11}$, and R$_{10}$CONHR$_{11}$;

$X_1$ and $X_2$, are the same or different from each other, are selected from the group consisting of —$CONR_8$, —$NR_8CO$—, —$CH_2NR_8$—, —$SO_2NR_8$—, wherein $R_8$ is selected from the group consisting of hydrogen or an alkyl-chain, linear or modified, containing from 1 to 6 carbon atoms;

$X_3$ is selected from the group consisting of —$CONR_7$, and —$NR_7CO$—, and $R_7$ is selected from the group consisting of an alkyl radical with no more than 15 carbon atoms;

$R_1$, $R_2$ and $R_3$, independently from each other, are hydrogen, halogen, or OR$_{12}$ wherein R$_{12}$ is selected from the group consisting of hydrogen, —$CH_2O(CH_2)_2OCH_3$ or —$CH_2O(CH_2)_2OCH_2CH_3$;

A is CH; n is a number from 0 to 2;

$R_5$ and $R_6$ are, independently from each other, selected from the group consisting of an aryl-alkyl radical containing no more than 15 carbon atoms, wherein the aryl moiety is selected from the group consisting of biphenyl, benzene, and naphtene, optionally substituted on the ring with one or more substituents, independently from each other, selected from the group consisting of halogen, an alkyl-radical containing from 1 to 6 carbon atoms, optionally substituted with no more than three fluorine atoms, an oxyalkyl-radical containing from 1 to 6 carbon atoms, optionally substituted with no more than three fluorine atoms, an —$NH_2$, —$NHR_{11}$, —$OR_{10}$, —$N(R_{10})_2$, —$CONHR_{10}$, —$COR_{10}$, —$COOR_{10}$, —$R_{10}COOR_{11}$, —$OR_{10}COOR_{11}$, —$CONHR_{10}$, —$R_{10}CONHR_{11}$, —NHCOR$_{10}$, nitro-radicals, wherein R$_{10}$ and R$_{11}$, are hydrogen or an alkyl-radical, linear or branched, containing from 1 to 6 carbon atoms with the proviso that R$_{10}$ cannot be H in the case of R$_{10}$COOR$_{11}$, OR$_{10}$COOR$_{11}$ and R$_{10}$CONHR$_{11}$.

2. Compound according to claim 1 wherein the alkyl-radical is selected from the group consisting of methyl, ethyl, propyl, butyl and pentyl and the halogen is selected from the group consisting of fluorine, chlorine, bromine and iodine.

3. Compound of general formula (I) according to claim 1 as herein defined:
   i) 1-N-[N(benzoyl)-1-amino-cyclohexancarbonyl]-amino-1-[N(methyl)N(2-phenylacetyl)]amino-2(2-naphthyl)ethane
   ii) 1-N-[N(4-methyl-benzoyl)-1-amino-cyclohexancarbonyl]-amino-1-[N(methyl)N(2-phenylacetyl)]amino-2(2-naphthyl)ethane
   iii) 1-N-[N(4-metoxy-benzoyl)-1-amino-cyclohexancarbonyl]-amino-1-[N(methyl)N(2-phenylacetyl)]amino-2(2-naphthyl)ethane
   iv) 1-N-[N(4-chloro-benzoyl)-1-amino-cyclohexancarbonyl]-amino-1-[N(methyl)N(2-phenylacetyl)]amino-2(2-naphthyl)ethane
   v) 1-N-[N(3,4-chloro-benzoyl)-1-amino-cyclohexancarbonyl]-amino-1-[N(methyl)N(2-phenylacetyl)]amino-2(2-naphthyl)ethane.

4. Pharmaceutical composition comprising as active principle a therapeutically effective amount of compound of formula (I) according to claim 1.

* * * * *